_United States Patent_ [19]

Chen et al.

[11] 4,100,218

[45] Jul. 11, 1978

[54] ETHANE CONVERSION PROCESS

[75] Inventors: Nai Yuen Chen, Titusville; Werner O. Haag, Lawrenceville, both of N.J.

[73] Assignee: Mobil Oil Corporation, New York, N.Y.

[21] Appl. No.: 801,713

[22] Filed: May 31, 1977

[51] Int. Cl.$^2$ .................. C07C 15/02; C07C 11/04; C10G 37/02
[52] U.S. Cl. ..................... 260/673; 208/67; 260/70; 208/71; 208/75; 260/683 R
[58] Field of Search ............. 260/673, 683 R; 208/67, 208/70, 138, 135

[56] References Cited

U.S. PATENT DOCUMENTS

| | | | |
|---|---|---|---|
| 3,760,024 | 9/1973 | Cattanach | 260/673 |
| 3,928,483 | 12/1975 | Chang et al. | 260/668 R |

OTHER PUBLICATIONS

Encyclopedia of Chem. Tech., 8503–8514 (1965), Kirk-Othmer.

*Primary Examiner*—Delbert E. Gantz
*Assistant Examiner*—G. E. Schmitkons
*Attorney, Agent, or Firm*—Charles A. Huggett; Carl D. Farnsworth

[57] ABSTRACT

Ethane is converted to LPG and gasoline and/or aromatics concentrate in a combination process which comprises directly passing olefin effluent from the thermal cracking of ethane over a special crystalline aluminosilicate zeolite of the ZSM-5 type and recovering aromatics and $C_3+$ hydrocarbons. For best yields, the thermal cracking step is conducted under more severe conditions than are used when ethylene production is optimized. The second, olefin conversion step is carried out at either the same pressure as the cracking step or higher. The process is of particular interest where low cost ethane is available.

14 Claims, 2 Drawing Figures

ETHANE CONVERSION PROCESS

BACKGROUND OF THE INVENTION

1. Field of the Invention

The present invention is concerned with an improved ethane conversion process. More particularly, this concept deals with a novel processing scheme to convert light gases such as ethane to aromatics an $C_3+$ hydrocarbons.

2. Description of the Prior Art

Ethylene is commonly produced by steam pyrolysis or thermal cracking of hydrocarbons, particularly of ethane. Pyrolysis reactor operation conditions and feedstock properties control the composition of the product mixture. High selectivity for the desired product (i.e., ethylene) and minimum coke production are promoted by operating at high temperatures, short residence times, and low hydrocarbon partial pressures. The pyrolysis is usually conducted at pressures close to atmospheric (e.g., from about 20 to 40 p.s.i.g.) and at process temperatures from about 1300° to 1600° F. Many types of pyrolysis reactors are known in the art including fired tubular heaters, pebble-bed heaters, and regenerative furnaces, but fired tubular heaters are the generally preferred type of reactor. Single-pass conversions in these known processes are usually from 55 to 65 percent. When ethane is employed as the feedstock, ethylene yields of less than 50 percent are typical. Accordingly, recycling is employed to maximize the ethylene yield. When processing light hydrocarbon feedstocks such as ethane, ultimate yields of approximately 80 weight percent are possible with recycle cracking if once-through conversion is kept below 60 percent with low pressure operation. Steam is added to the hydrocarbon feed to reduce the hydrocarbon partial pressure; steam-to-hydrocarbon feed ratios are generally 0.1–0.4:1 on a weight basis for light hydrocarbon feedstocks such as ethane and propane.

Following thermal cracking, the effluent from the pyrolysis reactor must be rapidly cooled to a temperature at which no additional reaction occurs. This rapid cooling may be effected by various means, such as by directly admixing the effluent with a cool liquid or by indirect heat exchange or by combinations of these means. Ordinarily, it is desirable to first cool the effluent in transfer line exchangers which generate heat pressure steam and then further cool the exchanged effluent by a direct water quench in a quench tower.

Recovery, separation, and purification of the pyrolysis products are major elements of conventional ethylene manufacturing processes. The system must treat not only a full range of hydrocarbons such as hydrogen, methane, ethylene, ethane, propylene, propane, butylenes-butanes, and $C_5-400°$ F gasoline, but also minor contaminants such as acid gases, acetylene, propadiene, and hydrocarbon polymers. Broadly, there are three principal separations to be made following the quench and heat recovery system discussed above: (1) gasoline and heavier fractions from the $C_4$ and lighter hydrocarbons; (2) methane and hydrogen off-gases from the ethylene and heavier hydrocarbons; and (3) ethylene from ethane and the heavier hydrocarbons. These are difficult separations, usually accomplished by low-temperature, high-pressure straight fractionation.

Process flow descriptions and diagrams for typical ethylene manufacturing plants are presented in the 1975 *Petrochemical Handbook*, Hydrocarbon Processing 54(11): pp. 141–43, November, 1975. A more general discussion of thermal cracking of hydrocarbons to produce ethylene is presented in *Encyclopedia of Chemical Technology*, ed. by Kirk and Othmer, Vol. 8, 1965, pp. 503–514.

It has also been known for some time that synthetic zeolites may be suitably used to produce high yields of $C_3+$ hydrocarbons containing a substantial quantity of aromatics from a variety of hydrocarbon feedstocks. For example, U.S. Pat. No. 3,760,024 discloses a process for the preparation of aromatic compounds which involves contacting a feed consisting essentially of $C_2-C_4$ paraffins and/or olefins with a crystalline aluminosilicate of the ZSM-5 type at a temperature of 100° to 700° C, a pressure of 0–1000 psig, a WHSV of 0.5–400, and a hydrogen to hydrocarbon ratio of 0–20 and recovering the aromatics produced.

SUMMARY OF THE INVENTION

The present invention combines single-pass thermal cracking of ethane to produce an olefin-rich effluent with subsequent processing of thermal cracker effluent over a special type of crystalline aluminosilicate zeolite catalyst (i.e., of the ZSM-5 type) to produce aromatics and $C_3+$ hydrocarbons. This processing scheme allows further processing of the cooled effluent from the pyrolysis reactors of the ethylene plant without first separating or purifying the pyrolysis products. Conversion of the ethylene plant effluent to useful $C_3+$ products can exceed 95 weight percent of the $C_2= + C_3+$ components.

Integration of thermal cracking of ethane with ZSM-5 catalytic conversion according to the process of this invention eliminates the expensive separation and purification facilities normally associated with ethylene production and also saves the energy required for feed preparation in processes such as the ZSM-5 conversion process disclosed in U.S. Pat. No. 3,760,024 (discussed above). Effluent from ethane pyrolysis reactors contains not only ethylene but also hydrogen, methane, propylene, butene, and other components such as butadiene. Still other impurities usually present in crude ethylene streams are water, oxygen, carbon monoxide, nitrogen oxide, acetylene, organic acids, aldehydes, and sulfur compounds. These impurities are normally not present in feeds to processes such as that described in the '024 patent. Their removal from the ethane crack effluent to produce a pure ethylene stream is not only costly, but requires a very considerable amount of energy. See Stanford Research Institute Report No. 29 (1967) and No. 29A, pp. 203–208 (1971). The process of the present invention converts these impure streams to useful products over a ZSM-5 type catalyst without prior separation or purification of the cooled effluent from the pyrolysis reactor.

Conventional processes for the thermal cracking of ethane operate at about 60 percent conversion per pass in order to maximize ethylene selectivity. However, since the function of the thermal cracker in the present invention is to produce aromatizables, the thermal cracker should be operated above 60 percent conversion per pass. The objective of the thermal cracker in this processing scheme is to maximize single-pass conversion of ethane and to maximize total olefin and $C_5+$ yield, rather than to maximize ethylene yield. Accordingly, typical single-pass ethane conversions in the thermal cracking zone of this invention are above 75 percent. This is achieved by increasing the pyrolysis temperature or reactant residence time or both above the temperatures and/or residence times employed in conventional ethylene manufacturing plants.

Mild, low-temperature conversion of the ethylene plant effluent over the special crystalline aluminosilicate zeolite at temperatures between about 600° F to about 800° to 850° F, pressures between about 0 to 200 psig, and from 1–10 W.H.S.V. may be conducted in the presence of part or all of the quench water used in the ethylene process. In fact, it is expected that this water will actually decrease coking rates and lengthen catalyst cycles. When the ZSM-5 catalytic conversion is carried out at temperatures greater than about 800° to 850° F, BTX formation is favored but the water content of the ethylene plant effluent fed to the catalytic olefin conversion zone must be reduced to below 1 percent to prevent excessive catalyst aging.

This concept may also be described as a method of converting hard-to-transport light hydrocarbons to easily transportable products. This feature of the invention is particularly valuable in situations where the source of such light hydrocarbons is far away from the point of consumption. For example, in Saudi Arabia an abundance of ethane currently valued at about 1¢/pound is available for disposal. The "disposal" process of this invention produces more than 64 pounds of useful $C_3+$ products per 100 pounds of ethane charged. Moreover, only 2 pounds/100 pounds ethane is lost to coke and the remaining 34 pounds/100 pounds ethane is fuel of similar value to the original ethane. Also, of particular interest is the high $iC_4:nC_4$ ratio in the product gas: there is a worldwide shortage of $iC_4$ for alkylate. Finally, the production of 99 octane (R+O) naphtha is noteworthy: this aspect of the invention could become particularly valuable as unleaded octane pool requirements are raised.

In a special embodiment of this invention, the objective of maximizing benzene production and minimizing $C_2$ and lighter by-products is accomplished by further integrating the process scheme described above with a catalytic and/or thermal dealkylation unit.

DETAILED DESCRIPTION OF THE INVENTION

Figure 1:
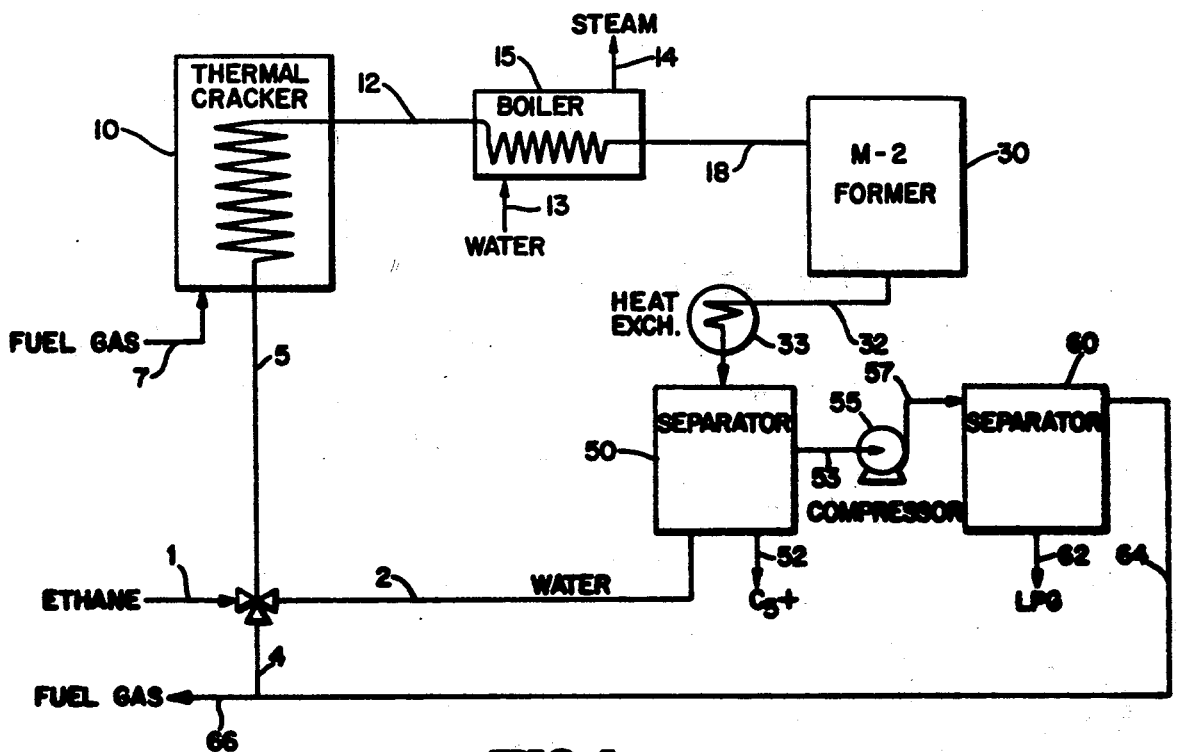
FIGS. 1 and 2 are schematic flow diagrams of two embodiments of the ethane conversion process of this invention. In the embodiment shown by FIG. 1, the second, olefin conversion step is carried out at the same pressure as the first, thermal cracking step and separation of LPG from light fuel gases is achieved by cooling and compressing the effluent from the separator of the olefin conversion step. In the alternative embodiment shown by FIG. 2, the effluent from the thermal cracker (i.e., the first, olefin formation step) is cooled via heat exchangers and compressed to 100 to 200 psig. Water is separated at this point and recycled to the thermal cracker. The stream is then reheated and sent to the second, olefin conversion step.

Referring now to FIG. 1, a combined stream of ethane fed via line 1, water (steam) fed via line 2, and if desired, recycled light fuel gases returned via line 4 pass through line 5 to thermal cracker 10, a tubular heater fired by fuel gas fed via line 7. Ethane is converted to an olefin-rich stream 12 at reaction conditions including temperatures of about 1500°–1600° F, pressures of 20–50 psig, and steam:ethane molar ratios of 0.1–0.7:1.

The higher steam:ethane molar ratios (i.e., from 0.4–0.7:1) are particularly useful when the pyrolysis temperature is in the higher range (i.e., from 1550° to 1600° F). The olefin-rich stream flows via line 12 to heat exchanger 15 which cools the olefin-rich stream to about 600°–1200° F (preferably 700°–1000° F) and generates high pressure steam (withdrawn via line 14) from the cooling water entering the exchanger via line 13. The high pressure steam withdrawn via line 14 is used in a separate power generation cycle (not shown). Furthermore, if desired, a small portion of stream 14 may be used to provide the dilution steam needed in stream 5 or to provide make-up water for stream 2 to compensate for losses.

The cooled, olefin-rich stream then passes through line 18 to the "M-2 Former" 30 wherein it is converted to useful $C_3+$ products over a special type of crystalline aluminosilicate zeolite catalyst which is desired in detail below. The products from M-2 Former 30 flow via line 32 through exchanger 33 where the products are further cooled and then to separator section 50. There a separation is made to recover a $C_5+$ fraction withdrawn through line 52, a $C_4-$ fraction withdrawn through line 53, and water which may be recycled via lines 2 and 5 to the thermal cracker 10.

The $C_4-$ fraction withdrawn from separator section 50 passes through line 53 to compressor 55. The compressed (100–200 psig) $C_4-$ fraction then flows via line 57 to separation section 60 where LPG product (withdrawn through line 62) is separated from light fuel gases (withdrawn through line 64). The light fuel gas passing through line 64 may be either withdrawn from the process via line 66 and employed as fuel or recycled to the thermal cracker via lines 4 and 5.

Figure 2:
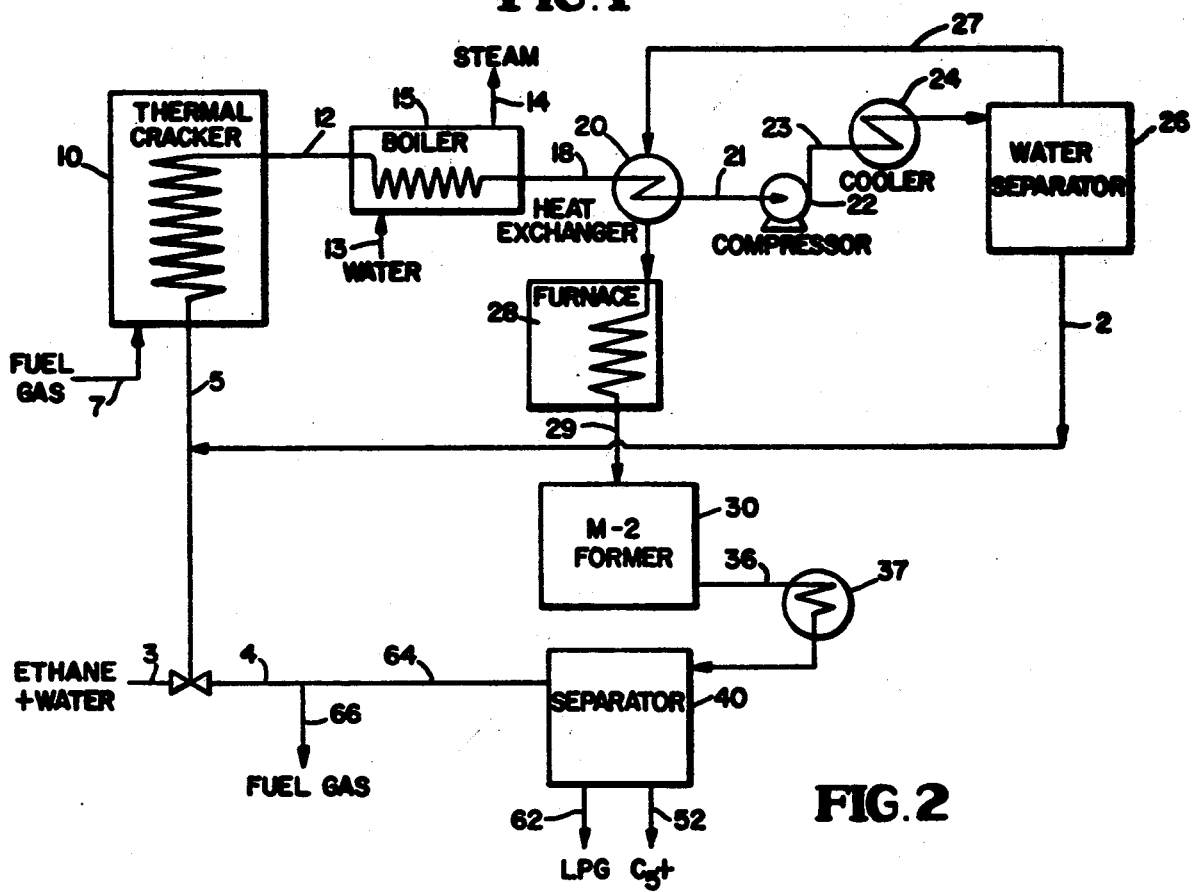

FIG. 2 is a flow diagram of an alternate embodiment of the process of this invention which is similar to that of FIG. 1 except for the product separation scheme and operating pressure of the M-2 Former 30. Referring now to FIG. 2, the cooled, olefin-rich stream from exchanger 15 passes via line 18 through heat exchanger 20 wherein it is further cooled to a temperature within the range from about 150° to 250° F and then passes via line 21 to compressor 22 where the stream is compressed to 100–200 psig. The compressed, olefin-rich stream passes via line 23 through cooler 24 to water separator 26 to condense and separate water from the olefin-rich stream. Process and mechanical design conditions are carefully selected to minimize formation and deposition of polymers. If desired the compressed gas may be further dried by contacting the alumina or molecular sieves. Separated water is recycled to the thermal cracker 10 through line 2. The compressed, dried, olefin-rich stream passes via line 27 through heat exchanger 20 to furnace 28 where it is reheated to 600°–1200° F and passes via line 29 to M-2 Former 30. The products from the M-2 Former 30 flow via line 36 through exchanger 37 where the products are cooled and then to separator section 40. There a separation is made to recover a $C_5+$ fraction withdrawn through line 52, LPG product withdrawn through line 62, and light fuel gases (e.g., hydrogen, methane, and ethane) withdrawn through line 64. As in the embodiment shown in FIG. 1, the light fuel gas passing through line 64 may be either withdrawn from the process via line 66 and employed as fuel or recycled via line 4 to combine with ethane and water fed via line 3 and pass via line 5 to the thermal cracker 10.

In either of the above-described embodiments, the C$_5$+ fraction withdrawn via line 52 is a valuable gasoline product high in aromatics. However, if benzene instead of gasoline is the desired product, an aromatics concentrate may be separated from the M-2 Former product and fed to a catalytic and/or thermal dealkylation unit in which the side chains are removed either as ethylene or as methane and ethane. The gaseous product of the dealkylation unit may be burned as fuel gas or recycled to the thermal cracker 10. Any dealkylation process known in the art may be employed. For example, thermal dealkylation in the presence of hydrogen at pressures of from 35 to 70 atmospheres, temperatures of from 600° to 750° C, and from 3 to 12 mole H$_2$/mole feed will produce single pass yields of benzene of about 80 to 90 weight percent. As a further example, catalytic dealkylation at pressures of from 35 to 60 atmospheres, temperatures of from 500° to 650° C, from 3 to 10 mole H$_2$/mole feed, and from 0.25 to 2.5 WHSV may be employed. Any known hydrodealkylation catalyst may be employed including chromia-alumina, cobalt-molybdenumalumina, nickel-alumina, silica-alumina, molybdenum-alumina, nickel-chromia-alumina, cobalt-chromium-molybdenum-alumina, and rhodium or ruthenium or chromia or alumina. As a final example, steam dealkylation processes are suitable for the production of benzene from th C$_5$+ fraction withdrawn via line 52.

Aromatic or BTX formation is favored if the ZSM-5 catalytic conversion is carried out in the M-2 Former 30 at temperatures greater than about 800° to 850° F, but the water content of the olefin-rich feedstream entering M-2 Former must then be reduced to less than 1 percent in orer to prevent excessive aging of the special type of crystalline aluminosilicate zeolite catalyst employed therein. This is possible according to the process scheme shown in FIG. 2 and described above. However, in a preferred embodiment of this invention, the temperature of the M-2 Former is maintained within the range from about 700° to about 800° to 850° F. It is further preferred to operate the M-2 Former between about 1-2 WHSV.

The special crystalline aluminosilicate zeolite catalysts referred to herein are members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful as catalysts in this invention possess, in combination: a silica to alumina ratio of at least about 12; and a structure providing constrained access to the crystalline-free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be ,perative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10 percent and 60 percent. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38. |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above-defined range of 1 to 12.

Thus, it should be understood that the "Constraint Index" value as used herein is an inclusive rather than an exclusive value. That is a zeolite when tested by any combination of conditions within the testing definition set forth herein above to have a constraint index of 1 to 12 is intened to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. Pat. application Ser. No. 358,192, filed May 7, 1973, (now abandoned) the entire contents of which are incorporated herein by reference, describes a zeolite composition, and a method of making such, designated as ZSM-21 which is useful in this invention.

U.S. Pat. application Ser. No. 528,061, filed Nov. 29, 1974, (now U.S. Pat. No. 4,016,265) the entire contents of which are incorporated herein by reference, describes a zeolite composition including a method of making it. This composition is designated ZSM-35 and is useful in this invention.

U.S. Pat. application Ser. No. 528,060, filed Nov. 29, 1974, (refiled as Ser. No. 560,412 now U.S. Pat. No. 4,046,859) the entire contents of which are incorporated herein by reference, describes a zeolite composition including a method of making it. This composition is designated ZSM-38 and is useful in this invention.

The X-ray diffraction pattern of ZSM-21 appears to be generic to that of ZSM-35 and ZSM-38. Either or all of these zeolites is considered to be within the scope of this invention.

The specific zeolites described, when prepared in the presence of organic cations, are substantially catalytically inactive, possibly because the intracrystalline-free space is occupied by organic cations from the forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below above 1.6 grams per cubic centimeter. It has been found that zeolites which satisfy all three of these criteria are most desired. Therefore, the preferred catalysts of this invention are those comprising zeolites having a constraint index as defined above about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967" published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZXM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

As has heretofore been stated, the most preferred form of the specific, previously defined zeolites in carrying out the novel process of this invention is the hydrogen form. As is well known in the art, the hydrogen form can be made by base exchanging the particular zeolite with hydrogen ions or ions capable of conversion to hydrogen ions, i.e., ammonium ions.

The crystalline zeolitic compositions can also be admixed with a non-acidic inorganic binder, such as alumina in order to impart the desired properties to the zeolite, such as increased strength and attrition resistance. Quite obviously, the proportion of binder employed is not narrowly critical, and it has been found convenient to use compositions where the binder is present from about 10 to 70 percent and preferably 30–40 percent based on the total weight of zeolite plus binder.

Furthermore, a hydrogenation/dehydrogenation material may be associated with the crystalline aluminosilicate zeolite. In this connection, it has been found that the presence of a hydrogenation metal prolongs catalyst life and leads to more efficient and desirable operation. A typical hydrogenation component would include tungsten, vanadium, molybdenum rhenium, nickel, cobalt, chromium, manganese, platinum, palladium, etc., including components thereof. The manner in which the hydrogenation component is associated with the zeolite is open. It can be base exchanged into the zeolite or impregnated therein or physically intimately admixed therewith. Particularly at M-2 forming temperatures in excess of about 800° F, improved product distributions are obtained by employing a zinc-containing HZSM-5 type catalyst. Conversely, commercial HZSM-5 extrudate is a satisfactory catalyst for low temperature (i.e., from about 700° to about 800°–850° F) conversion of olefins.

The following examples illustrate the best mode now contemplated for carrying out the invention.

EXAMPLES 1-2

Reaction conditions for the thermal cracking of ethane are: 1500°–1600° F, 20–50 psig, steam/ethane molar ratio of 0.1–0.7. Typical compositions of the effluent (excluding $H_2O$) from the thermal cracker in single-pass and extinction operation are shown in Table I.

TABLE I

| | Product Composition from Thermal Cracking of Ethane, Wt.% | |
|---|---|---|
| | 75% Conversion | Extinction Yield |
| $H_2$ | 4.7 | 5.8 |
| $CH_4$ | 5.1 | 7.2 |
| $C_2H_2$ | 0.9 | 2.3 |
| $C_2H_4$ | 57.1 | 79.8 |
| $C_2H_6$ | 25.0 | — |
| $C_3H_6$ | 1.8 | 2.0 |
| $C_3H_8$ | 0 | — |
| $C_4+$ | 5.4 | 2.9 |

EXAMPLES 3-4

Conditions for contacting the olefin-rich effluent from the thermal cracker with the special type of crystalline alumino-silicate zeolite described above are: 600°–1200° F, 0–200 psig, and 1–10 WHSV. Typical product distributions of the effluent from the M-2 Former when the thermal cracker is in single-pass and extinction operation are shown in Table II.

TABLE II

| | M-2 Former Product Distribution | |
|---|---|---|
| | 75% Ethane Conversion | Ethane Extinction |
| $H_2 + C_1 + C_2$ | 36.3 | 15.0 |
| $C_3 + C_4$ | 26.0 | 35.5 |
| $C_5$ + Gasoline | 37.7 | 49.5 |

Thus a yield of 85 lbs. of LPG and gasoline can be produced from 100 lbs of ethane.

EXAMPLES 5-7

Ethylene was subjected to three experiments involving conversion over a HZSM-5 type crystalline aluminosilicate catalyst at atmospheric pressure. Comparisons of yields and product distribution for low and high temperature operation, with and without zinc, were made. The results are summarized in Table III.

TABLE III

| | Ethylene Conversions Over HZSM-5 | | |
|---|---|---|---|
| | Catalysts | | Zn(0.4%) Exchanged |
| Catalyst | HZSM-5(B) Extrudate | HZSM-5(B) Extrudate | HZSM-5 (no binder) |
| Process Conditions | | | |
| Temp., ° F (max) | 775 | 950 | 950 |
| Temp., ° F (av) | 650 | 875 | 875 |

TABLE III-continued

| | Ethylene Conversions Over HZSM-5 | | |
|---|---|---|---|
| | Catalysts | | Zn(0.4%) Exchanged |
| Catalyst | HZSM-5(B) Extrudate | HZSM-5(B) Extrudate | HZSM-5 (no binder) |
| WHSV | 1.0 | 1.0 | 1.0 |
| $C_2=$ Conv. | 99 | 99 | 99 |
| Products lb/100 lb $C_2=$ | | | |
| $C_1 + C_2$ (Fuel) | 3 | 11 | 10 |
| $C_3$ (LPG) | 12 | 23 | 16 |
| $iC_4$ | 15 | 9 | 5 |
| $nC_4$ | 7[1] | 5 | 3 |
| $C_5 + NA$[4] | 24[1] | 5 | 1 |
| Arom. (Benzoid) | 38[1] | 45[2] | 62[3] |
| Naphthalenes, etc. | 1[1] | 2 | 3 |
| Aromatics Comp., lb/100 lb $C_2=$ | | | |
| BTX, total | 16 | 35 | 57 |
| Benzene | 1 | 4 | 12 |
| Toluene | 6 | 16 | 30 |
| Xylenes | 9 | 15 | 15 |
| Trimethylbz | 3 | 4 | 2 |
| Tetramethylbz | 1 | 2 | 1 |
| Total Ethylbz | 18 | 4 | 2 |

[1] The combined fractions represent a 70 percent yield of 99 octane (R+O) gasoline product.
[2] Dealkylation of this fraction yields 30 lbs. benzene/100 lbs. $C_2=$.
[3] Dealkylation of this fraction yields 52 lbs. benzene/100 lbs. $C_2=$.
[4] NA = non-aromatics.

What is claimed is:
1. An ethane conversion process which comprises:
   a. thermally cracking ethane at temperatures within the range from about 1500° to 1600° F, pressures within the range from about 20 to 50 psig, and steam:ethane molar ratios within the range from about 0.1–0.7:1 to produce an olefin-rich effluent in a thermal cracker wherein the ethane conversion is greater than about 60 weight percent;
   b. cooling the olefin-rich effluent to a temperature within the range from about 600° to 1200° F;
   c. contacting the cooled, olefin-rich effluent, without prior separation or purification, at a pressure within the range from about 0 to 200 psig and a WHSV of from about 1 to 10 with a crystalline aluminosilicate zeolite characterized by a pore dimension greater than about 5 Angstroms, a silica to alumina ratio of at least 12 and a constraint index within the range of from 1 to 12; and
   d. recovering a $C_5+$ product suitable for use as gasoline, an LPG product, and light fuel gases.
2. The process of claim 1 wherein at least a portion of the light fuel gases are recycled to the thermal cracking step.
3. The process of claim 1 wherein the crystalline aluminosilicate zeolite has been exchanged with hydrogen ions or ammonium ions.
4. The process of claim 3 wherein a hydrogenation/dehydrogenation component is associated with the crystalline aluminosilicate.
5. The process of claim 4 wherein the hydrogenation/dehydrogenation component is zinc.
6. The process of claim 1 wherein the ethane conversion in the thermal cracker is greater than 75 percent.
7. The process of claim 1 wherein at least a portion of the recovered $C_5+$ product is further treated by separating an aromatics concentrate.
8. The process of claim 7 wherein the separated aromatics concentrate is dealkylated and a benzene product is recovered from the dealkylated aromatics concentrate.
9. The process of claim 1 wherein at least a portion of the water in the olefin-rich effluent is separated therefrom prior to contacting said olefin-rich effluent with the crystalline aluminosilicate zeolite.
10. A method for converting ethane to LPG and gasoline which comprises:
   a. thermally cracking ethane at temperatures within the range from about 1500° to 1600° F, pressures within the range from about 20 to 50 psig, and steam:ethane molar ratios within the range from about 0.1–0.7:1 to produce an olefin-rich effluent in a thermal cracker wherein the ethane conversion is greater than about 60 weight percent;
   b. cooling the olefin-rich effluent to a temperature within the range from about 600° to about 800° to 850° F;
   c. contacting the cooled, olefin-rich effluent, without prior separation or purification, at a pressure within the range from about 0 to 200 psig and a WHSV of from about 1 to 10 with a crystalline aluminosilicate zeolite which has been exchanged with hydrogen ions or ammonium ions and which is characterized by a pore dimension greater than about 5 Angstroms, a silica to alumina ratio of at least 12, and a constraint index within the range of from 1 to 12; and
   d. recovering a $C_5+$ gasoline product, a $C_3 + C_4$ LPG product, and light fuel gases.
11. The process of claim 10 wherein the ethane conversion in the thermal cracker is greater than 75 percent.
12. A method for converting ethane to LPG and aromatics which comprises:
   a. thermally cracking ethane at temperatures within the range from about 1500° to 1600° F, pressures within the range from about 20 to 50 psig, and steam:ethane molar ratios within the range from about 0.1–0.7 to produce an olefin-rich effluent in a thermal cracker wherein the ethane conversion is greater than about 60 weight percent;
   b. cooling and compressing the olefin-rich effluent to a temperature within the range from about 80° to 120° F and to a pressure within the range from about 100 to 200 psig;
   c. drying the cooled, olefin-rich effluent;

d. contacting the dried, olefin-rich effluent, without further prior separation or purification, at a temperature within the range from about 800° to about 1200° F, at a pressure within the range from about 100 to 200 psig, and a WHSV of from about 1 to 10 with a zinc-containing crystalline aluminosilicate zeolite which has been exchanged with hydrogen ions or ammonium ions and which is characterized by a pore dimension greater than about 5 Angstroms, a silica to alumina ratio of at least 12, and a constraint index within the range of from 1 to 12; and e. recovering a $C_5+$ fraction, a $C_3 + C_4$ LPG product, and light fuel gases; and f. separating an aromatics concentrate from the $C_5+$ fraction.

13. The process of claim 12 wherein the separated aromatics concentrate is dealkylated and a benzene product is recovered from the dealkylated aromatics concentrate.

14. The process of claim 12 wherein the ethane conversion in the thermal cracker is greater than 75 percent.

* * * * *

UNITED STATES PATENT AND TRADEMARK OFFICE
CERTIFICATE OF CORRECTION

PATENT NO. : 4,100,218
DATED : July 11, 1978
INVENTOR(S) : Nai Yuen Chen and Werner O. Haag It is certified that error appears in the above-identified patent and that said Letters Patent are hereby corrected as shown below:

| Col. | Line | Correction |
|---|---|---|
| 1 | 9 | "an" should be "and" |
| 1 | 47 | "heat" should be "high" |
| 2 | 47 | "crack" should be "cracker" |
| 3 | 63 | "recycled" should be "recycle" |
| 4 | 18 | "desired" should be "described" |
| 4 | 51 | "the" should be "with" |
| 5 | 21-22 | "molybdenumalumina" should be "molybdenum alumina" |
| 5 | 27 | "th" should be "the" |
| 5 | 34 | "orer" should be "order" |
| 6 | 47 | ",perative" should be "operative" |
| 7 | 66 | "4,016,265" should be "4,016,245" |
| 8 | 56 | "above" should be "about" |
| 9 | 26 | "ZXM" should be "ZSM" |
| 9 | 57-58 | "aluminosiicate" should be "aluminosilicate" |
| 10 | 3 | "components" should be "compounds" |
| 10 | 63 | "Catalysts" should be underlined |
| 11 | 3 | "Catalysts" should be underlined |
| 11 | 21 | There should be space after "Xylenes" |

Signed and Sealed this

Second Day of January 1979

[SEAL]

Attest:

RUTH C. MASON
Attesting Officer

DONALD W. BANNER
Commissioner of Patents and Trademarks